(12) United States Patent
Ferko, III (10) Patent No.: US 9,072,577 B1
(45) Date of Patent: Jul. 7, 2015

(54) PORTABLE MEDICAL COOLING ASSEMBLY

(76) Inventor: Joseph G. Ferko, III, Pasadena, MD (US)

( * ) Notice: Subject to any disclaimer, the term of this patent is extended or adjusted under 35 U.S.C. 154(b) by 560 days.

(21) Appl. No.: 12/955,526

(22) Filed: Nov. 29, 2010

(51) Int. Cl.
*A61F 7/00* (2006.01)
*A61F 7/02* (2006.01)

(52) U.S. Cl.
CPC ........... *A61F 7/00* (2013.01); *A61F 2007/0054* (2013.01); *A61F 2007/0056* (2013.01); *A61F 2007/023* (2013.01); *A61F 2007/022* (2013.01); *A61F 2007/003* (2013.01); *A61F 2007/0001* (2013.01); *A61F 7/0097* (2013.01); *A61F 2007/0002* (2013.01); *A61F 2007/0018* (2013.01); *A61F 2007/0008* (2013.01); *A61F 2007/0009* (2013.01)

(58) Field of Classification Search
USPC .......................................... 607/96–112; 2/458
See application file for complete search history.

(56) References Cited

U.S. PATENT DOCUMENTS

| | | | | |
|---|---|---|---|---|
| 3,134,891 | A * | 5/1964 | Hyer | 219/211 |
| 3,738,367 | A * | 6/1973 | Hardy | 607/104 |
| 4,729,598 | A | 3/1988 | Hess | |
| 5,269,369 | A | 12/1993 | Faghri | |
| 5,305,471 | A * | 4/1994 | Steele et al. | 2/102 |
| 5,486,207 | A * | 1/1996 | Mahawili | 607/104 |
| 6,682,550 | B2 | 1/2004 | Clifton et al. | |
| 6,730,115 | B1 | 5/2004 | Heaton | |
| 6,878,156 | B1 * | 4/2005 | Noda | 607/106 |
| 6,969,399 | B2 | 11/2005 | Schock et al. | |
| 7,089,995 | B2 | 8/2006 | Koscheyev et al. | |
| 7,179,279 | B2 | 2/2007 | Radons et al. | |
| 7,527,612 | B1 | 5/2009 | Carpenter et al. | |
| 7,565,705 | B2 | 7/2009 | Elkins et al. | |
| 2002/0153126 | A1 * | 10/2002 | Clemente | 165/46 |
| 2006/0247745 | A1 * | 11/2006 | Thompson | 607/108 |
| 2009/0005840 | A1 | 1/2009 | Harty | |
| 2009/0048590 | A1 * | 2/2009 | Conrad et al. | 606/28 |
| 2009/0264969 | A1 * | 10/2009 | Gammons | 607/104 |
| 2010/0204764 | A1 | 8/2010 | Garetz | |

OTHER PUBLICATIONS

Minh, Nguyen Q. Improved Vapour Compression Refrigeration Cycles: Literature Review and Their Application to Heat Pumps. Tech. Purdue University, Jul. 17, 2006. Web. Mar. 19, 2013. <http://docs.lib.purdue.edu/>, "Minh".*

* cited by examiner

*Primary Examiner* — Joseph Stoklosa
*Assistant Examiner* — Adam Avigan
(74) *Attorney, Agent, or Firm* — Roylance, Abrams, Berdo & Goodman, L.L.P.

(57) ABSTRACT

A cooling assembly is provided for cooling selected parts of the body of a patient to treat hyperthermia or to induce mild hypothermia in the treatment of strokes. The assembly includes a self-contained cooling unit containing a water supply, a battery operated refrigeration unit and circulating pump. A cooling member is connected to the cooling unit and is adapted for receiving cooled water and contacting selected parts of the patient to cool the patient. The cooling member can be a vest, wrap, blanket, chair, hood or cap.

9 Claims, 10 Drawing Sheets

PORTABLE MEDICAL COOLING ASSEMBLY

FIELD OF THE INVENTION

The present invention is directed to a portable cooling assembly for cooling a patient. The invention is particularly directed to an assembly including a cooling unit coupled to a garment for cooling a patient.

BACKGROUND OF THE INVENTION

There are situations where a person can become overheated such that the body temperature rises above an acceptable level. Overheating of the body can result in heat exhaustion, heat stroke and occasionally death. When the body temperature rises above an acceptable level, it is desirable to cool the body quickly.

In recent years, it has been found that inducing mild hypothermia following cardiac arrest can reduce the consequences of cardiac arrest including reducing damage to vital organs. Inducing mild hypothermia in stroke victims immediately after the stroke has also been found beneficial in reducing the damage to the brain.

Various attempts have been made to cool down a person and replenish fluids. The methods of cooling the body have included spraying the body with water, applying ice packs and using fans. However, care must be taken to prevent shock caused by cooling too rapidly.

Numerous devices have been proposed for cooling a body. One example uses a pad or cover that can be placed on or under the patient and receives a cooling fluid. Examples of this kind of cooling device are disclosed in U.S. Pat. No. 6,730,115 to Heaton, U.S. Pat. No. 6,969,399 to Schock et al., U.S. Pat. No. 6,682,550 to Clifton et al., and U.S. Patent Publication No. 2009/0005840 to Harty. U.S. Pat. No. 4,729,598 to Hess discloses a chair having an air sack receiving cool air.

Other cooling devices in the form of a garment for cooling selected portions of the body are also known. Examples of these devices are disclosed in U.S. Pat. No. 5,269,369 to Faghri, U.S. Pat. No. 7,089,995 to Koscheyev et al., U.S. Pat. No. 7,179,279 to Radons et al., U.S. Pat. No. 7,527,612 to Carpenter et al., U.S. Pat. No. 7,565,705 to Elkins et al., and U.S. Patent Publication No. 2010/0204764 to Garetz.

While the prior devices have been acceptable for their intended use, there is a continuing need in the industry for improved cooling apparatus.

SUMMARY OF THE INVENTION

The present invention is directed to a portable cooling assembly adapted for cooling a patient. The invention is particularly directed to a portable liquid cooling apparatus for connecting to a cooling garment in contact with the patient for cooling the patient.

Accordingly, one aspect of the invention is to provide a portable cooling assembly that is able to lower the core body temperature of a patient. The assembly is able to lower the body temperature and cooling the patient quickly and efficiently in a controlled manner. The assembly is able to induce mild hypothermia to treat a patient after cardiac arrest or stroke.

The cooling apparatus of the invention is a self-contained unit containing a water supply and a refrigeration unit for cooling the water. The cooling apparatus has a pump system that is able to circulate the cooling water through a cooling garment and return the water to the assembly in a continuous cycle to continuously cool the patient to a desired level. The unit can be controlled by a thermostat to control the water temperature.

The cooling apparatus includes a removable battery to operate the assembly on battery power. The apparatus also includes a transfer switch to enable operation of the assembly by AC current from a household outlet or generator.

Another aspect of the invention is to provide a cooling apparatus having a thermostat to adjust the temperature of the water to a selected temperature for circulating through a garment or other device to cool the patient in a controlled manner.

A further aspect of the invention is to provide a cooling garment adapted for coupling to a cooling apparatus for receiving cooling water to cool the body temperature of a patient. The garment is constructed to receive the cooling water through passages or tubes that cover the surfaces of the garment to cool selected portions of the patient. The tubes receiving the cooling water can be concentrated in selected areas and spaced further apart in other areas to control the amount of cooling to the different areas of the patient.

Another aspect of the invention is to provide a cooling garment having cooling tubes with an inlet end and an outlet end with a self-closing valve to retain water within the tubes of the garment.

The various objects and advantages of the invention are attained by providing a cooling garment in the form of a blanket, pad, vest, wrap, jacket or hood that can be coupled to a cooling apparatus for receiving cooling water. In another embodiment, the cooling unit can be connected to a cooling device that is able to cool an article or device.

These and other aspects and advantages of the invention are basically attained by providing a cooling assembly for cooling a patient comprising a portable integral cooling unit for supplying cooled water. The cooling unit has a water reservoir, a refrigeration unit for cooling water in the reservoir, an inlet having a coupling with a self-closing valve to prevent leakage, an outlet having a coupling with a self-closing valve to prevent leakage, a battery source for operating the refrigeration unit, and a circulating pump for circulating cooled water between the inlet and outlet. A cooling member directly contacts the patient. The cooling member has at least one tube on an inner surface of the cooling member. The tube has a length to contact a selected part of the body. The tube has a first end defining an inlet and a second end defining an outlet. A supply tube has a first feed tube connecting the outlet of the cooling unit to the inlet of the garment. A second feed tube connects the inlet of the cooling unit to the outlet of the garment, and an insulating sleeve surrounding the first and second supply tubes.

The advantages of the invention are also attained by providing a method of cooling a selected part of a patient. A portable integral cooling unit is provided for supplying cooled fluid and having a fluid inlet and a fluid outlet. A plurality of garments are provided having different shapes for cooling different parts of the patient. Each of the garments has at least one tube attached thereto for receiving cooling fluid and having a fluid inlet and a fluid outlet. One of the plurality of garments is selected and the garment is placed on the patient. The selected garment is connected to the inlet and outlet of the cooling unit. Cooling fluid from the cooling unit circulates to the selected garment and cools the patient.

The advantages of the invention are further attained by providing a cooling garment for cooling selected parts of a patient. The garment comprises a back portion having a dimension to cover the back of the patient. The back portion has a first tube arranged in a circuitous pattern for receiving cooling water and has an inlet and an outlet. A first front portion has a first side edge connected to a first side of the back portion and has a second tube arranged in a circuitous pattern for receiving cooling water and has an inlet and an outlet. A second front portion has a first side edge connected to a second side of the back portion and has a third tube arranged in a circuitous pattern for receiving cooling water and has an inlet and an outlet. A first shoulder flap has a first edge connected to a top edge of the back portion and has a fourth tube arranged in a circuitous pattern for receiving cooling water and has an inlet end and an outlet end. The first shoulder flap has a fastener and is adapted for folding over a first shoulder of the patient and fastens to the first front portion. A second shoulder flap has a first side edge connected to a top edge of the back portion and has a fifth tube arranged in a circuitous pattern for receiving cooling water and has a first inlet end and a second outlet end. The second shoulder flap has a fastener and is adapted for folding over a second shoulder of the patient and fastens to the second front portion. Each of the inlets and outlets of the tubes is adapted for coupling directly to a cooling water supply for receiving cooling water to cool the patient.

These and other features of the invention will become apparent from the following detailed description of the invention which, in conjunction with the annexed drawings, disclose various embodiments of the invention.

BRIEF DESCRIPTION OF THE DRAWINGS

The following is a brief description of the drawings, in which.

DETAILED DESCRIPTION OF THE INVENTION

Figure 1:
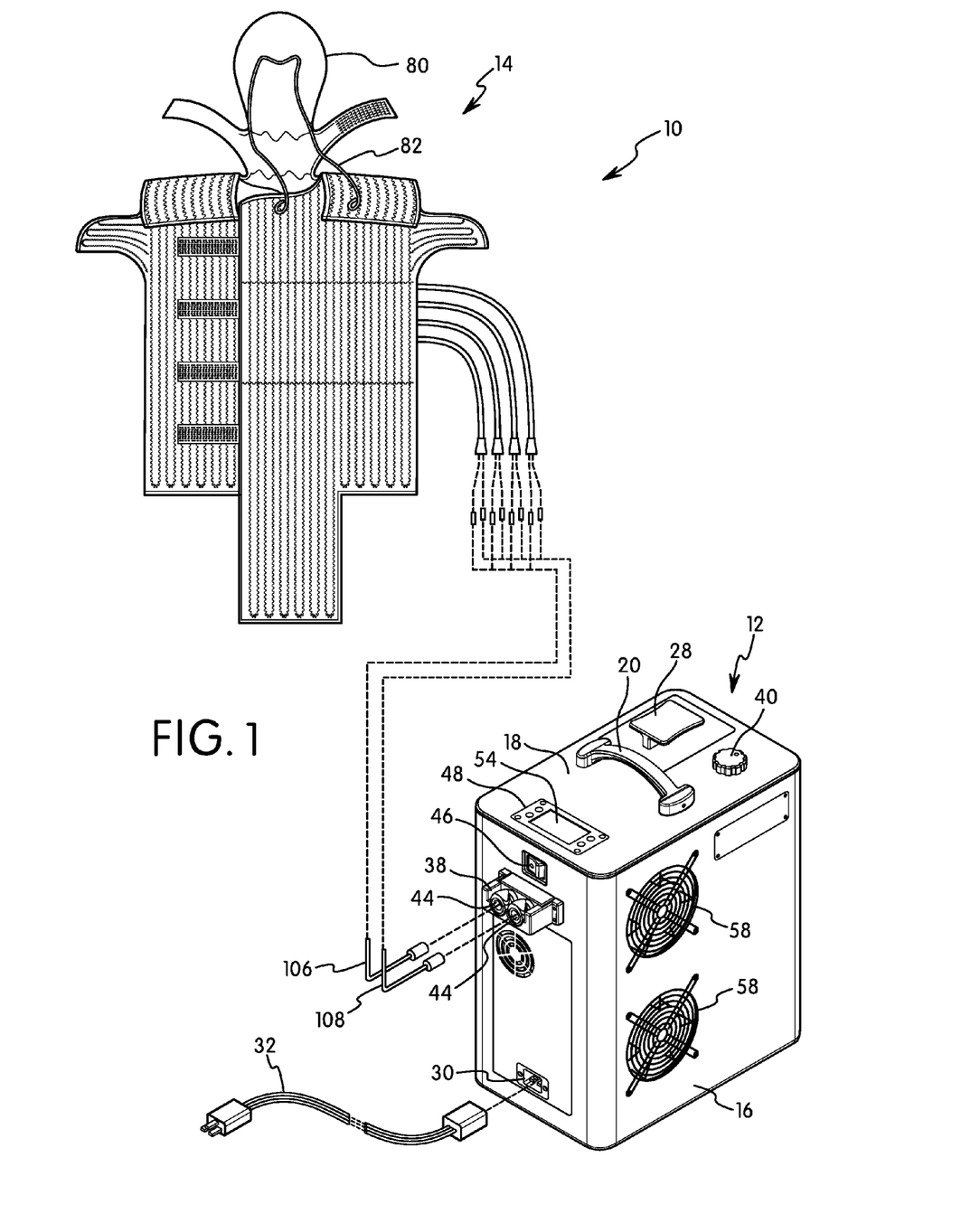
FIG. 1 is a perspective view of the cooling assembly.
Figure 1A:
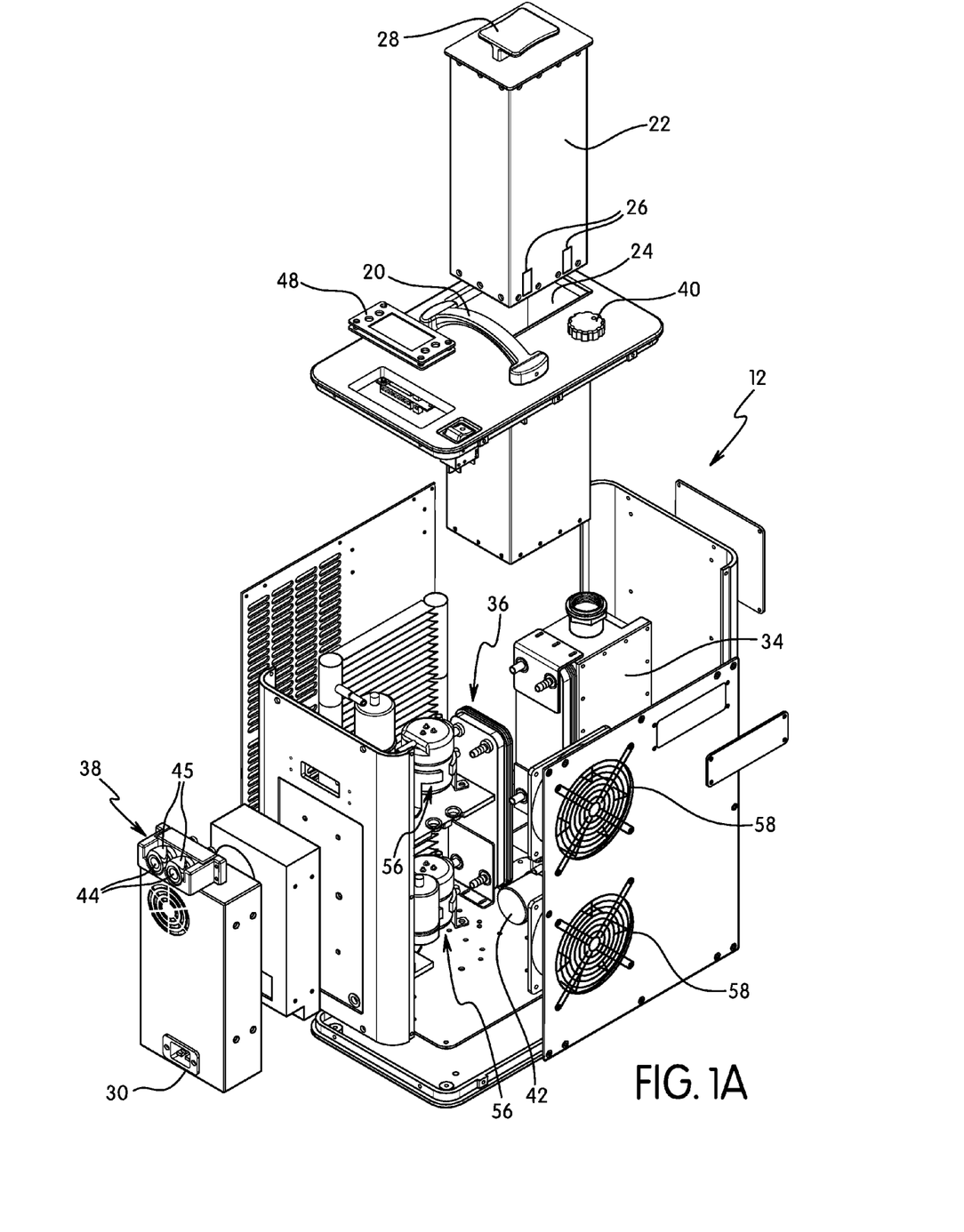
FIG. 1A is an exploded perspective view of the cooling apparatus in one embodiment of the invention.

The present invention is directed to a cooling assembly adapted for cooling the body temperature of a patient. The invention is particularly directed to a cooling assembly that includes a portable cooling unit that can be connected to a cooling device for cooling the patient. Referring to FIG. 1, the cooling assembly 10 of the invention includes a cooling unit 12 and at least one cooling device for cooling the patient. In the embodiment shown in FIG. 1, the cooling device is a cooling wrap 14.

The cooling assembly 10 is adapted for treating a patient suffering from hyperthermia or heat exhaustion to cool the patient. The assembly is also adapted for inducing mild hypothermia to a patient after cardiac arrest or a stroke.

The cooling unit 12 as shown in FIGS. 1-6 is a self contained portable unit including a housing 16 with a top wall 18. As shown in FIG. 1, top wall 18 has a handle 20 to allow for carrying of the unit.

The cooling unit 12 in preferred embodiments of the invention is a self contained assembly that is readily portable for operating in various environments and under different conditions and is able to circulate cooled water between the cooling unit and a cooling device. The cooling unit 12 includes a battery 22 for supplying electrical power to the unit when the cooling unit is operated in a battery mode. As shown in FIG. 1, the battery 22 is readily removable and is inserted through an opening 24 in the top wall 18. The battery 22 preferably includes contacts 26 which can be at the lower end for mating with corresponding contacts in the cooling unit. The battery preferably includes a handle 28 for quick removable and replacement of the battery. The battery 22 can be easily removed and replaced with a fully charged battery. The battery 22 can be removed and connected to a remote battery charger (not shown) to recharge the battery as needed. In preferred embodiments, the cooling unit 22 includes a self contained recharging unit for recharging the battery 22 when the cooling unit is connected to an external power source such as household current or a generator. The external power source can operate off the cooling unit 12 when the cooling unit is in an external power mode. In preferred embodiments, the battery is able to operate the cooling unit for about 2-4 hours.

Cooling unit 22 includes an electrical receptacle 30 or plug for connecting to an electrical cord 32. Electrical cord 32 is connected to a standard electrical outlet or other electrical supply such as a generator. An automatic transfer switch 46 is typically included to convert the operation of the cooling unit from an external AC power supply to the DC battery supply.

The cooling unit 12 in one preferred embodiment of the invention includes a water tank 34 forming a reservoir for the circulating water, a refrigeration unit 36 and an outlet 38. The water tank 34 is contained within the housing and includes a filler cap 40 shown in FIG. 1 for filling the water tank with water as needed. The water tank 34 is connected to the refrigeration unit 36. A pump 42 circulates the cooled water from the water tank 34 to the outlet 38 for circulating through the cooling wrap 14. As discussed below, the cooled water is circulated by the pump through the refrigeration unit and through the wrap 14 and returns the water back to the cooling unit.

Figure 2:
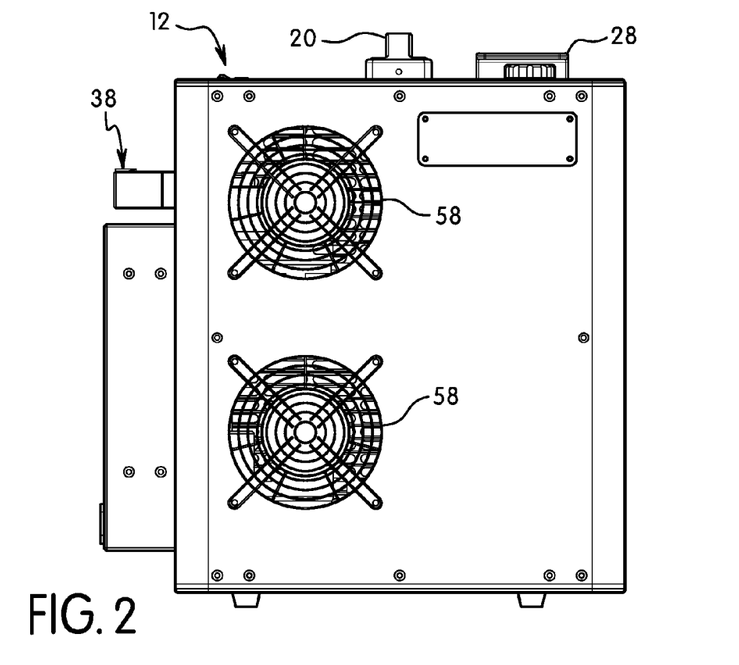
FIG. 2 is a right side view of the cooling apparatus.
Figure 3:
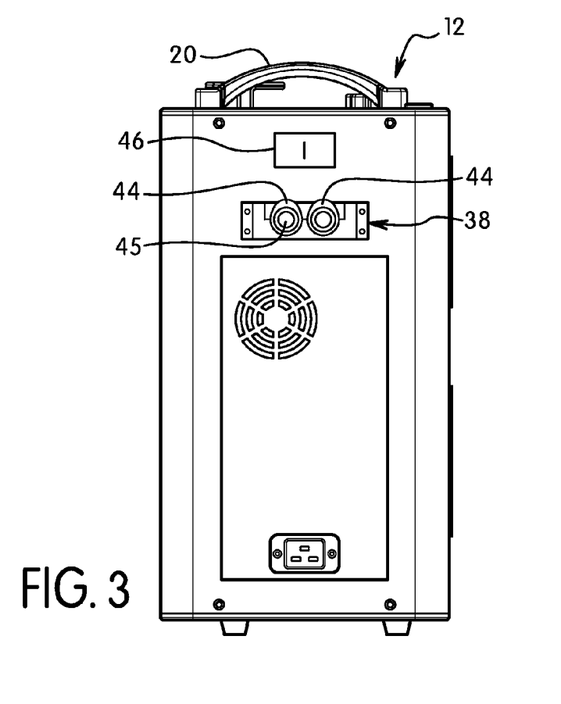
FIG. 3 is a front view of the cooling apparatus.
Figure 4:
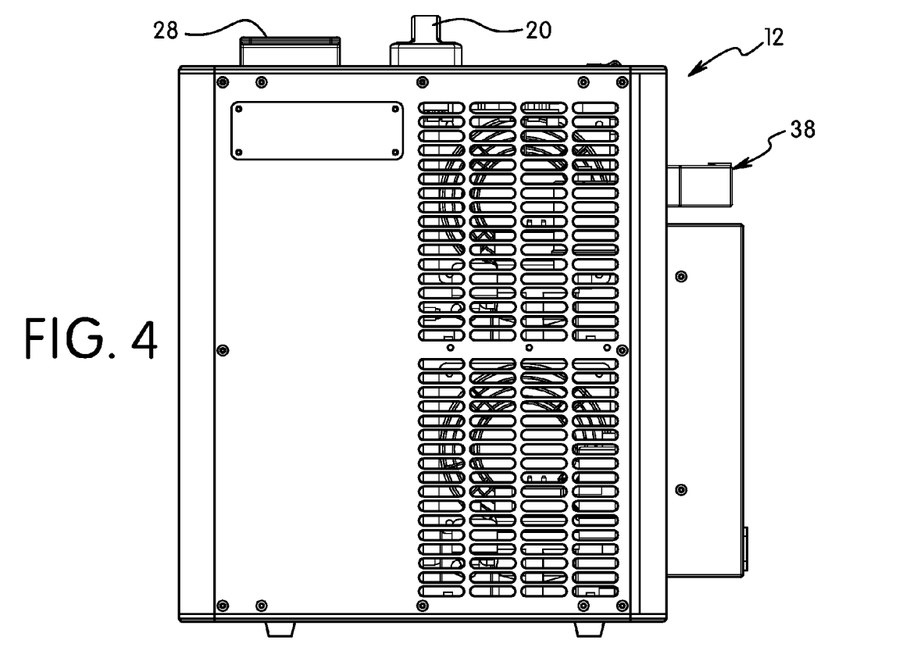
FIG. 4 is a left side view of the cooling apparatus.
Figure 5:
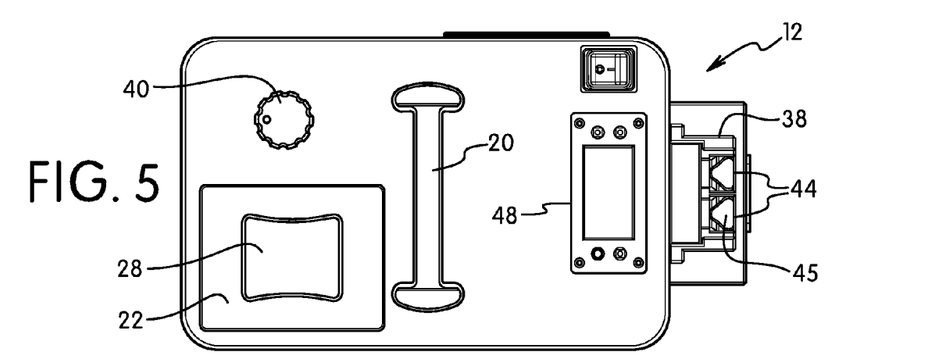
FIG. 5 is a top view of the cooling apparatus.

As shown in FIGS. 1-3, outlet 38 of cooling unit 12 has a pair of coupling members 44 forming an inlet and an outlet for the cooling water being supplied to the cooling garment. Each coupling 44 has a self closing valve 45 to prevent the water from leaking when the unit is not in use. The self closing valve of each coupling unit 44 is opened by inserting the coupling of a connecting tube that extends between the cooling unit and cooling device such as the cooling wrap 14.

Figure 6:
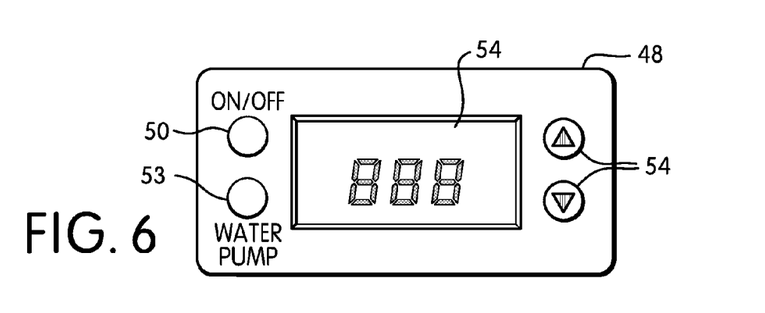
FIG. 6 is an enlarged view of the display screen of the cooling apparatus.

Cooling unit 12 includes an operating switch 46 for switching the unit between AC power and the battery power. A display panel 48 is provided on the top wall 18. Display panel 48 includes an actuating on/off button 50 to actuate the compressor to cool the water in the tank 22, a button 52 for setting the water temperature, an indicator light, an actuator pump switch 53 to actuate the circulating pump, and a display screen 54 for displaying the set water temperature and the actual water temperature.

The cooling assembly of the invention is adapted for use with various cooling garments or cooling devices that are capable of cooling the patient for treating heat exhaustion and hyperthermia. The cooling unit of the invention is also suitable for rapidly cooling the core temperature of a patient after stroke or cardiac arrest to induce mild hypothermia for transporting the patient to the medical facility.

The refrigeration unit 36 of the cooling unit 12 can operate on battery power or AC power as needed. Preferably, two compressors 56 are coupled in series to provide the necessary cooling of the water when operating under battery power. Battery power typically operates at 24 volts DC current. The compressors are also adapted for operating under AC current at 120 to 230 volts. Each compressor 56 includes a fan 58 for drawing air through the unit to dissipate the heat generated during the cooling of the water.

Figure 7:
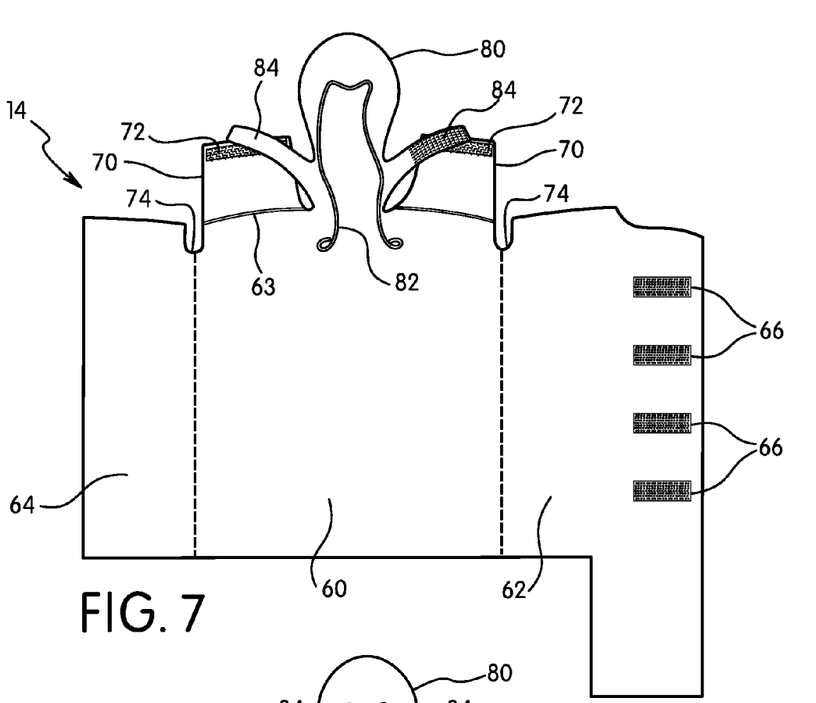
FIG. 7 is a top view of the cooling wrap in one embodiment of the invention showing the wrap in the open position.

In one embodiment of the invention, the cooling garment is a wrap 14 as shown in FIGS. 7-10. Wrap 14 has a shape and dimension to wrap around the chest and torso of the patient for rapidly cooling the vital organs of the patient. As shown in FIG. 7, the wrap 14 includes a back portion 60, a first side portion 62, and a second side portion 64. Back portion 60 has a width to cover substantially the entire back surface of the patient. First side portion 62 and second side portion 64 have complementing fasteners 66 for securing the wrap on the patient. The fasteners 66 in the embodiment illustrated are a conventional hook and loop type fastener for allowing adjustment and easy attachment and removal.

Back portion 60 has a top edge 68 with a pair of shoulder flaps 70 that can be folded over the tops of the shoulders of the patient and secured to the top edge of the first side portion 62 and the second side portion 64 by fasteners 72.

Figure 8:
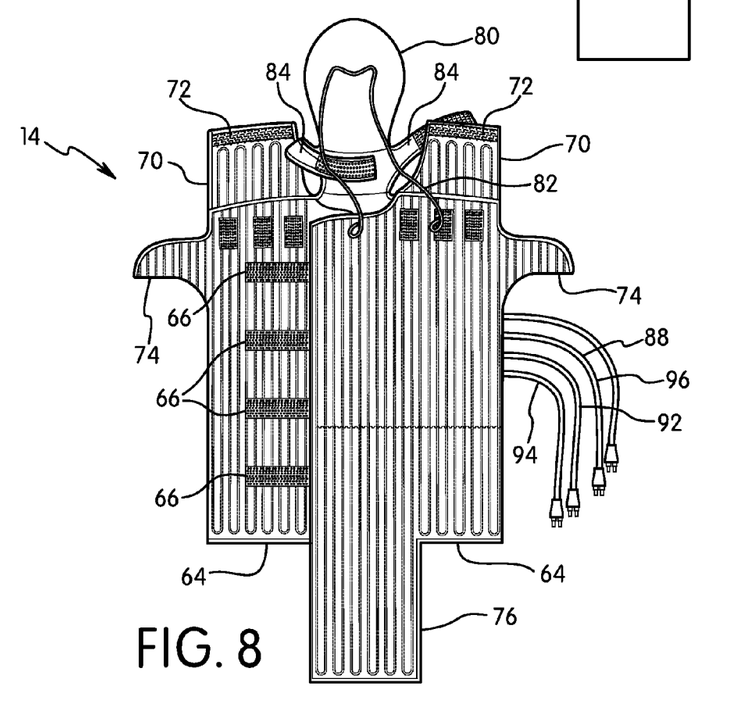
FIG. 8 is a top view of the cooling wrap of FIG. 7 which one side folded inward.
Figure 9:
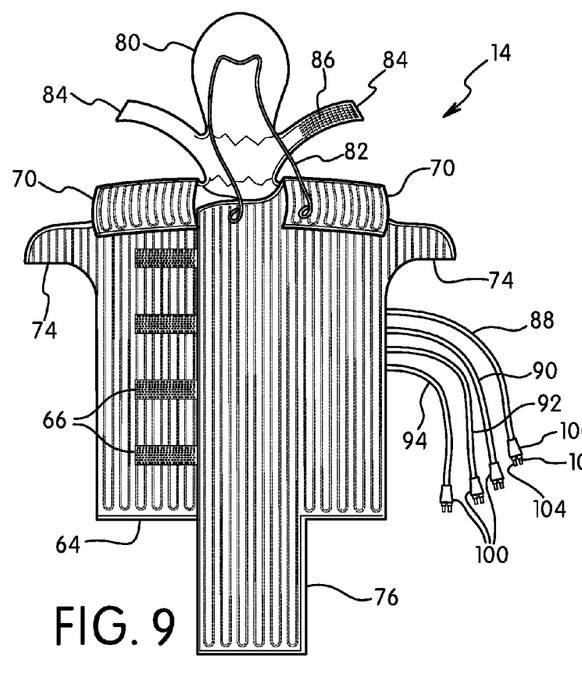
FIG. 9 is a top view of the cooling wrap of FIG. 7 showing both sides and the should flaps folded inward.
Figure 10:
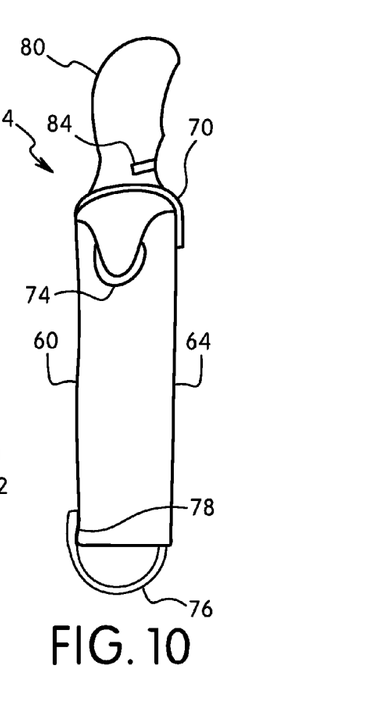
FIG. 10 is a side view of the cooling wrap in the operating position.

As shown in FIGS. 8, 9 and 10, an underarm portion is provided between the back portion 60 and the respective first front portion 62 and second front portion 64. Each underarm section 74 has a substantially U-shape as shown in FIG. 10 to extend outwardly from the back portion and the respective front portion. The underarm sections 74 have a length to cover the armpit of the patient and a portion of the underarm and width to wrap around at least a portion of the sides of the shoulder and arm. The underarm sections 74 preferably have a length to extend along the under side of the arm about 6-10 inches, although the length and width can vary.

The second front portion 64 as shown in FIG. 8 includes an extension 76 forming a groin portion having a width and length to wrap under the groin area of the patient. The extension portion includes fasteners that mate with fasteners on the back portion as shown in FIG. 10. The fasteners 78 are typically a hook and loop type fastener. Alternatively, the groin portion can be integrally formed with the back portion and folded forward to attach to the front portion 64 by fasteners.

As shown in FIGS. 8 and 9, the wrap 14 includes a plurality of cooling tubes for receiving the cooling water from the cooling unit. The cooling tubes in the preferred embodiment are flexible plastic tubes having an internal diameter of about ¼ inch and a laid out in a circuitous pattern to cover each portion of the wrap. In one embodiment, the tubes are attached to the inner surface of the wrap by stitching or an adhesive. As shown, the tubes are laid in a pattern to provide cooling to the various portions and surfaces of the cooling wrap 14.

In one embodiment, a hood 80 is connected to the back portion 60. The hood 80 has a shape to cover the top sides and back of the patient's head and includes a drawstring 82 to secure the hood and enclose the hood around the patient's head. The hood also includes a chin strap 84 to wrap around the neck of the patient under the chin. The chin strap 84 includes a hook and loop type fastener 86 to secure the chin strap around the neck of the patient. As shown in FIG. 9, the hood 80 and the chin strap 84 include cooling tubes for receiving the cooling water to cool the patient's head and neck.

In the embodiment illustrated, four supply tubes 88, 90, 92 and 94 are provided to circulate the cooling water throughout selected areas of the wrap 14. In other embodiments, fewer than four or more than four supply tubes can be provided. Each supply tube includes a feed end and a return end and is laid out in a circuitous pattern in selected portions of the wrap to define a cooling circuit. In the embodiment illustrated, supply tube 88 forms a circuit that extends to the hood 80, the shoulder flap 70 and the underarm portion 74. Supply tube 90 forms a circuit that extends to the second front portion 64 and the extension groin portion 76. Supply tube 92 forms a circuit that extends to the back portion 60. Supply tube 94 forms a circuit that extends to the first front portion 62 and the left underarm portion 74. Each supply tube is connected to the cooling unit to receive cooling water and circulate the water through the wrap to selectively cool portions of the patient.

Figure 11:
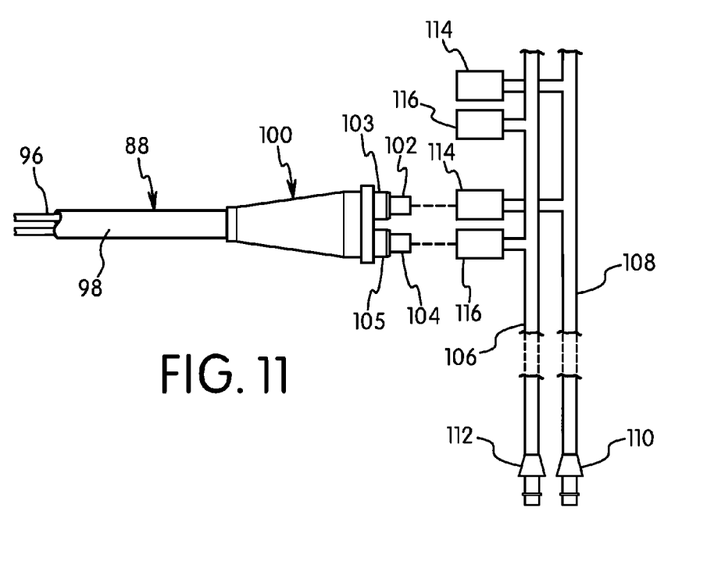
FIG. 11 is a top view of the supply tubes and feed tubes to the cooling garment.

The supply tubes are depicted in FIG. 11. Each supply tube includes a circulating tube 96 that forms a continuous loop through the selected portion of the wrap. Each supply tube includes an outer insulating shell 98 to minimize heat transfer between the cooling wrap and the cooling unit. The insulating shell 98 is provided only on the portions of the supply tube outside of the cooling wrap. Each circulating tube 96 of the supply tube terminates at a coupling 100 having an inlet 102 and an outlet 104. In FIG. 11, a single supply tube 88 is shown for simplicity. It will be understood that the supply tubes 88, 90, 92 and 94 are substantially the same and correspond to the structure of supply tube 88 as shown in FIG. 11. Preferably, the inlets 102 and outlets 104 have a self closing valve 103 and 105 that close when disconnected from the feed tubes 106 and 108 to retain water in the supply tubes.

Each supply tube is connected to a feed tube 106 and 108 for connecting to the cooling unit to carry cooled water and circulate cooled water through each supply tube and return the water to the cooling unit. The feed tubes 106 and 108 have a coupling end 110 and 112, respectively, for connecting to the cooling unit. Preferably, the couplings are snap in type couplings for quickly connecting the feed tubes to the cooling unit. In the embodiment shown, the feed tubes 106 and 108 form a manifold having a plurality of outlets 114 and 116, respectively, for coupling with the inlet and outlet of the supply tubes. In one embodiment, the outlets 114 and 116 include a self-closing valve or one way valve that are opened when the supply tubes are connected to the feed tubes.

The feed tubes include a sufficient number of outlets for connecting with each of the supply tubes of the respective garment. In the embodiment shown, the feed tubes will have four outlets for connecting with each of the four supply tubes of the wrap 14. Alternatively, each of the outlets of the feed tubes can be connected to a plurality of different cooling garments to simultaneously operate different garments for cooling more than one patient at a time. In other embodiments, the supply tubes can include a regulating flow valve.

The feed tubes 106 and 108 are connected to the couplings 44 of the cooling unit as shown in FIG. 1 and are connected to the respective supply tubes of the wrap 14. The cooling unit is then actuated to cool the water and circulate the cooled water continuously through the supply tubes and the wrap.

The wrap 14 has a shape and configuration for ease of attaching to a patient. As shown in FIG. 7, the wrap 14 can be laid substantially flat so that the patient can be rolled or placed directly on the wrap with the hood 80 positioned on the patient's head. The front portions are then wrapped around the body of the patient and secured by the fasteners 66. The extension groin section 76 can then be wrapped under the groin and attached to the back section by the fasteners. The hood 80 can be fitted onto the heat of the patient by the drawstring 82 and the chin strap 84 wrapped around the neck and secured by the fasteners. As shown, each section of the wrap includes cooling tubes for receiving the cooling water to cool selected portions of the body of the patient. In the embodiment illustrated, the groin section cools the blood flow passing through the groin area, the underarm portions cool the blood flow passing through the arms of the patient, and the hood and chin strap cool the head and the blood throughout flowing through the head and the neck of the patient.

Figure 12:
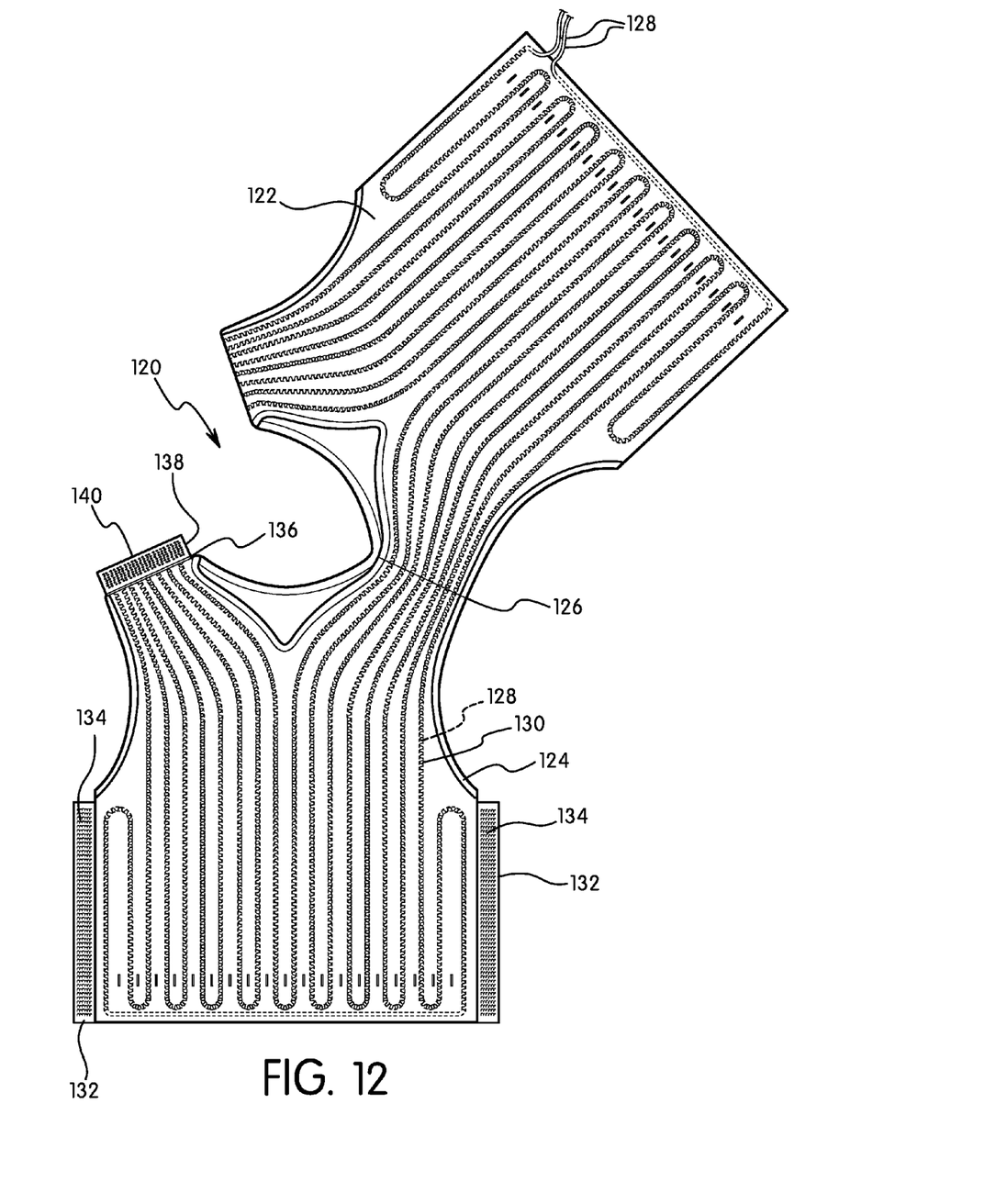
FIG. 12 is a top view of the cooling vest in one embodiment of the invention.
Figure 13:
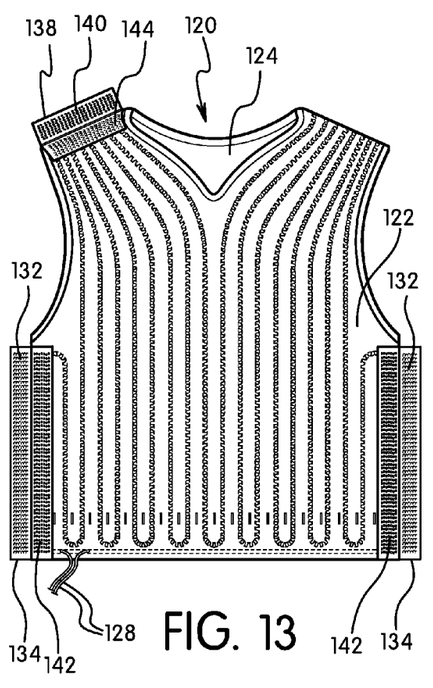
FIGS. 13 and 13A are front views of the cooling vest in the closed operating position.
Figure 13A:
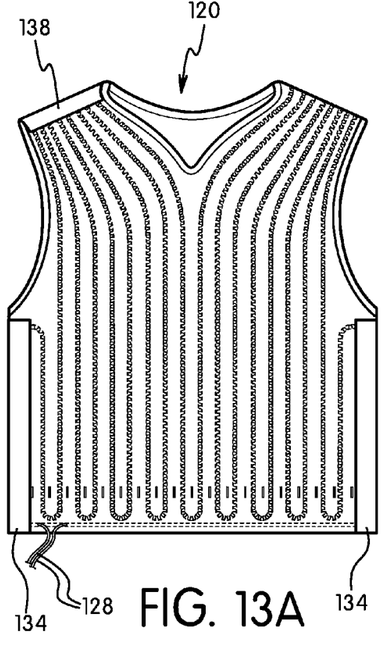

The cooling unit 12 is adapted for use with various cooling garments and cooling devices. In another embodiment shown in FIGS. 12 and 13, the cooling unit can be connected to a cooling vest 120. Vest 120 as shown in FIG. 12 has a front section 122 and a back section 124. The front section is connected to the back section by one shoulder portion 126. A cooling tube 128 extends in a circuitous path around the front section 122 and the back section 124 to provide the cooling effect to the patient. In the embodiment shown, the cooling tube 128 is attached to the vest by cross stitching 130, although other fastening means can be used.

Front section 122 includes side flaps 132 having a hook and pile type fastener 134. The open shoulder portion 136 also includes a flap having a fastener 140 such as a hook and pile fastener.

In use, the vest is placed over the patient and the side flaps 132 and the shoulder flap 136 are connected to the back portion 124 by complementing fasteners 142 and 144, respectively.

Figure 14:
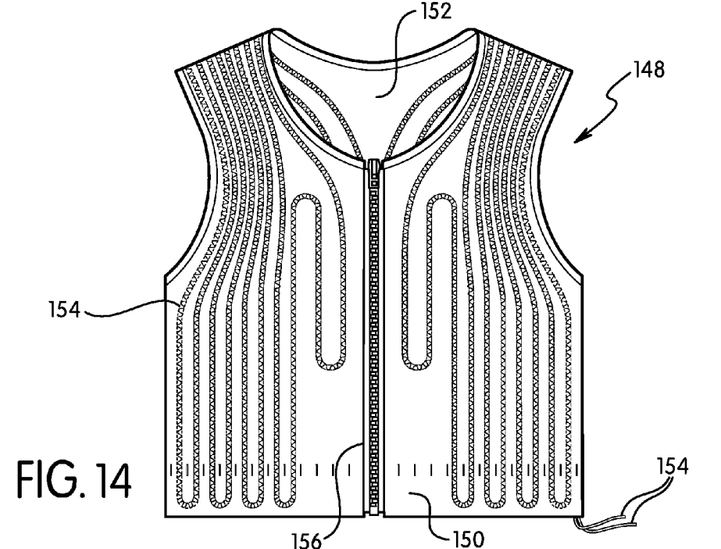
FIG. 14 is a front view of the vest in another embodiment.

In another embodiment shown in FIG. 14, a vest 148 has a front portion 50, a back portion 152, and a continuous tube 154 arranged in a circuitous path around the front and the back portions. The front portion 150 is provided with a zipper 156 to close the front portion and secure the vest 148 onto the patient. In another embodiment shown in FIGS. 15 and 16, the cooling device is a chair that can be connected directly to the cooling unit. The chair 160 has a frame 162, a seat portion 164, and a back portion 166. In a preferred embodiment, the frame 162 is collapsible or foldable to assist in transporting and storage.

Figure 15:
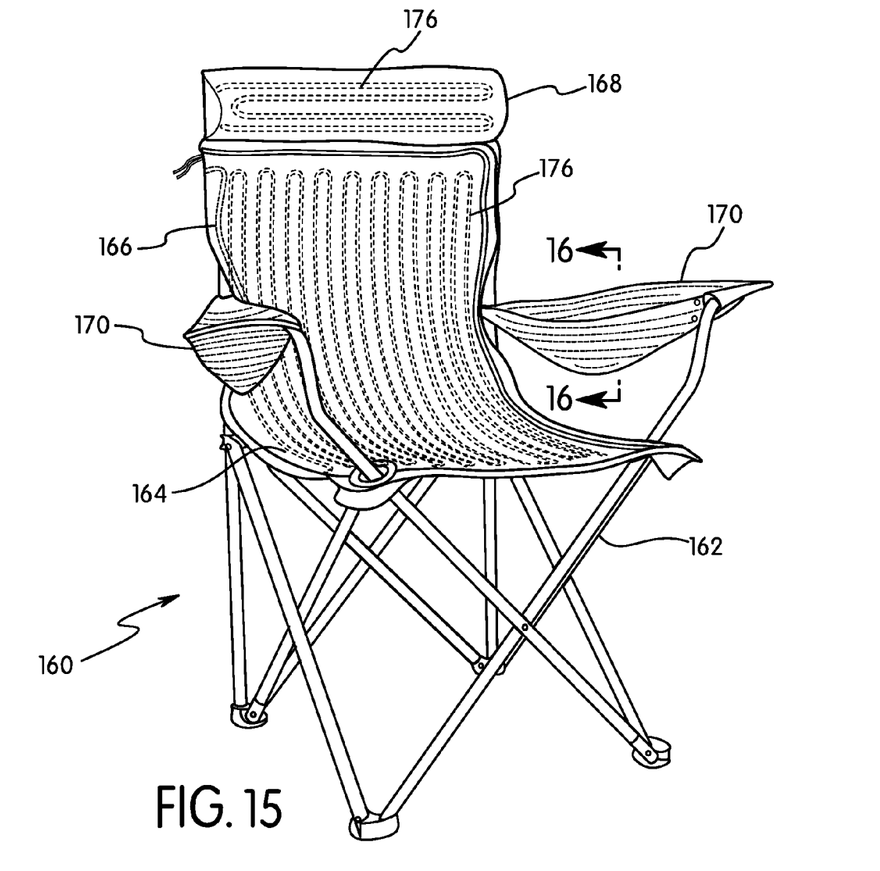
FIG. 15 is a perspective view of the cooling chair in another embodiment of the invention.

In the embodiment illustrated, the seat portion 164 and the back portion 166 are integrally formed together to form a continuous sling for supporting the patient. A head rest 168 is connected to the upper end of the back portion 166 for supporting the head and neck of the patient.

Figure 16:
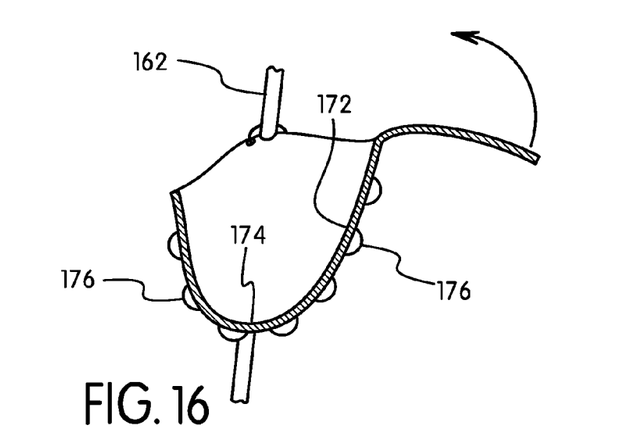
FIG. 16 is a cross-sectional view of the arm of the chair taken along line 16-16 of FIG. 15.

The chair 160 includes arm sections 170 for supporting the arms of the patient while seated in the chair. The arm sections are formed from a fabric and are connected to the frame 162 to form a sling having a substantially U-shaped interior surface as shown in FIG. 16. The arm sections 170 form side portions 172 and a bottom portion 174 having a shape and dimension to contact the bottom surface and side surfaces of the arms of the patient. A top flap 171 is provided that can be folded over the arm of the patient to assist in cooling the patient. A cooling tube 176 extends through the seat portion 164, back portion 166, head rest 168 and each arm section 170 in a circuitous manner to provide a cooling effect to the patient. The tube 176 preferably extends the entire length of each arm section 170 as shown in FIG. 15 to provide cooling of the bottom and sides of the arm of the patient.

Figure 17:
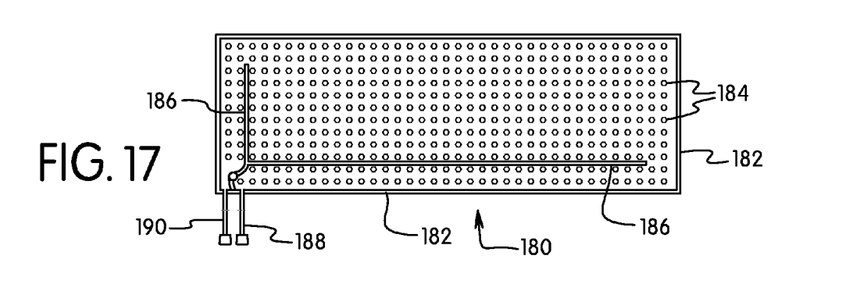
FIG. 17 is a top view of the cooling pad in another embodiment of the invention.

FIG. 17 shows a cooling pad 180 for connecting to the cooling unit. The cooling pad 180 is formed from top and bottom sheets that are sealed around the edges 182 and sealed at a plurality of points 184. A barrier 186 is formed by sealing the top and bottom sheets together to direct the cooling water from the inlet 188 to the outlet 190 so that the water circulates throughout the cooling pad. The cooling pad can be used as blanket or a pad placed under a patient. The cooling pad can also be used in a temporary or portable mortuary.

Figure 18:
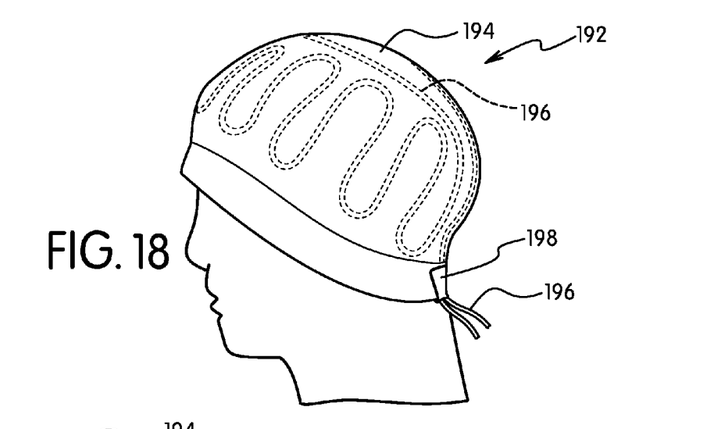
FIG. 18 is a side view of the cooling cap in another embodiment of the invention.
Figure 19:
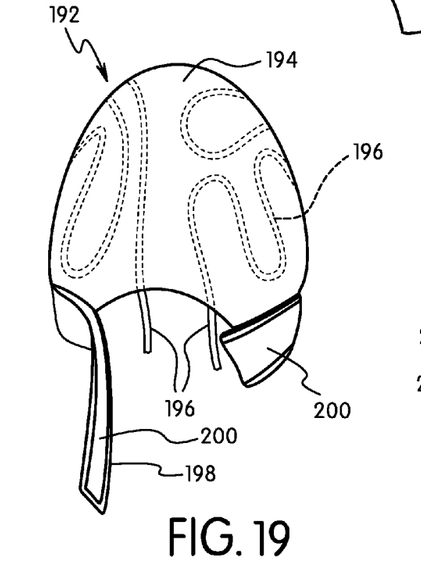
FIG. 19 is a rear view of the cooling cap of FIG. 18.

FIGS. 18 and 19 show a cooling cap for use in connection with the cooling unit. The cooling cap is made of a fabric and has a shape to fit over the head of the patient. The head portion 194 of the cap 192 includes a tube 196 arranged in a circuitous pattern around the sides and top portions of the head portion 194. A strap 198 extends from the bottom edge of the head portion 194 for securing the cap 192 to the head of the patient by a hook and loop type fastener 200.

Figure 20:
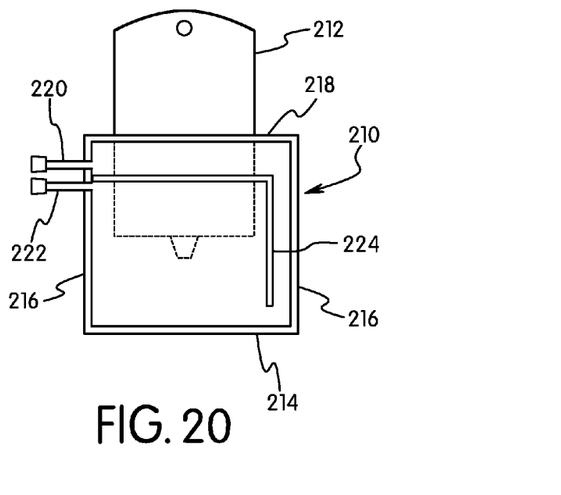
FIG. 20 is a front view of a cooling pouch in another embodiment of the invention.

In a further embodiment shown in FIG. 20, the cooling device is a pouch 210 forming an envelope to surround an article 212. The pouch 210 in the embodiment shown has two opposite walls formed from two sheets of plastic material joined together to form a bottom seam 214, opposite side seams 216 and an open end 218. Cooling supply tubes 220 and 222 are connected to the pouch to circulate cool water through the pouch. As in the previous embodiment, a divider 224 is provided between the two layers of each side wall. The ouch has a dimension to receive an article that needs to be cooled such as a medication. In the embodiment shown, the article 212 being cooled is an IV bag.

The cooling unit of the invention is interchangeable with a variety of cooling garments and cooling devices that are capable of cooling the body temperature of the patient. The cooling unit is capable of being connected to one or more of the cooling devices for cooling more than one patient at a time and for cooling different cooling devices simultaneously. The cooling unit is readily portable and can be operated by battery power or an external power supply. The unit is particularly adapted for use by emergency medical personnel to treat a patient suffering from hyperthermia and for inducing mild hyperthermia in a patient who has suffered a stroke or cardiac arrest.

In the embodiments shown, the cooling garments are formed from a fabric material that has flexible plastic tubes attached to the inner surface to be in contact with the patient. Alternatively, the garments can be made from two sheets of plastic material that are fused together to form channels for directing the water to selected areas.

While various embodiments have been chosen to illustrate the invention, it will be understood by one skilled in the art that various changes and modifications can be made without departing from the scope of the invention as defined in the appended claims.

What is claimed is:

1. A cooling assembly for cooling a patient, said assembly comprising:
- a portable integral cooling unit for supplying cooled water, said cooling unit having a water reservoir, a refrigeration unit for cooling water in the reservoir, an inlet having a coupling with a self-closing valve to prevent leakage, an outlet having a coupling with a self-closing valve to prevent leakage, a battery source for operating said refrigeration unit, and a circulating pump for circulating cooled water between said inlet and outlet;
- a cooling garment for directly contacting the patient, said cooling garment comprising
- a back portion having a first side edge, a second side edge, a top edge, and a tube arranged in a circuitous pattern for receiving said cooled water, said tube having an inlet and an outlet;
- a first front portion having a first side edge and a second side edge, said first side edge connected to said first side edge of said back portion and having a tube arranged in a circuitous pattern for receiving the cooled water and having an inlet and an outlet;
- a second front portion having a tube for receiving said cooling water, a first side edge connected to said second side edge of said back portion, and a second side edge, said first and second front portions having a width to overlap and having fasteners for removably fastening the first front portion to the second front portion;
- a first shoulder flap having a first edge connected to said top edge of said back portion adjacent said first side edge of said back portion and having a tube arranged in a circuitous pattern for receiving said cooled water and having an inlet and an outlet, said first shoulder flap being positioned for folding over a first shoulder of said patient and being removably fastened to said first front portion by a fastener; and
- a second shoulder flap having a first edge connected to a top edge of said back portion adjacent said second side edge of said back portion and positioned for folding over a second shoulder of said patient and being removably fastened to said second front portion by a fastener, said second shoulder flap having a tube arranged in a circuitous pattern to receive the cooled water;
- a bottom flap coupled to a bottom edge of said second front portion and adapted for folding under the groin of the patient and being removably fastened to said back portion by a fastener, said bottom flap including a tube for arranging in a circuitous pattern for receiving said cooled water;
- a first U-shaped flap having an open upper side and attached to a top of said first front portion and said back portion and having a tube for receiving said cooled water; and
- a second U-shaped flap having an open upper side and attached to a top of said second front portion and said back portion and having a tube for receiving said cooled water;
- said first U-shaped flap and second U-shaped flap having a dimension to cover an underarm area of the patient; and
- a supply tube having a first feed tube connecting the outlet of the cooling unit to an inlet of the tubes of said cooling garment, a second feed tube connecting the inlet of the cooling unit to an outlet of the tubes of said cooling garment for directing cooled water through the cooling garment, and an insulating sleeve surrounding the first and second supply tubes.

2. The assembly of claim 1, wherein
said tubes of said cooling garment include a coupling member with a self closing valve to retain water within said tubes when said tubes are disconnected from said cooling unit.

3. The assembly of claim 1, wherein
said cooling unit further comprises a first compressor unit and a second compressor unit connected in series for cooling said water.

4. The assembly of claim 1, wherein
said cooling unit further includes an electrical connector for connecting said cooling unit to an external power supply for operating said cooling unit and charging said battery.

5. The assembly of claim 1, wherein said garment further comprises
a hood attached to said back portion between said first shoulder flap and said second shoulder flap, said hood having opposite first and second side portions, a top portion and a chin strap forming a neck portion for covering the front and sides of the neck of the patient, and a cooling tube arranged in a circuitous pattern through said first and second side portions, top portion and chin strap for cooling the sides and top of the head of the patient and for cooling the neck of the patient.

6. The assembly of claim 5, wherein
said neck portion is attached to said first side portion and has a length to wrap around a front portion of the neck of the patient and removably fastened to the second side portion by a fastener.

7. The assembly of claim 1, wherein
said first U-shaped flap and second U-shaped flap have a length of about 6-10 inches to cover the bottom and sides of at least a portion of the arm of the patient.

8. The assembly of claim 1, further comprising
a manifold having a plurality of connectors for supplying said cooled water from said cooling unit simultaneously to a plurality of cooling garments.

9. A cooling assembly for cooling a patient, said assembly comprising:
- a portable integral cooling unit for supplying cooled water, said cooling unit having a water reservoir, a refrigeration unit for cooling water in the reservoir, an inlet having a coupling with a self-closing valve to prevent leakage, an outlet having a coupling with a self-closing valve to prevent leakage, a battery source for operating said refrigeration unit, and a circulating pump for circulating cooled water between said inlet and outlet;
- a cooling garment for directly contacting the patient, said cooling garment comprising:
- a back portion with a first side edge, a second side edge, a top edge, a bottom edge and a tube arranged in a circuitous pattern connected to said cooling unit for receiving said cooled water, said tube having an inlet and an outlet and a length to cool a back side of said patient;
- a first front portion having a first side edge and a second side edge, said first side edge connected to said first side edge of said back portion and a substantially U-shaped first underarm flap with an open upper side and coupled to a top edge of said first front portion and said back portion and having a tube arranged in a circuitous pattern for receiving the cooled water and having an inlet and an outlet connected to said cooling unit for cooling a front side and underarm of said patient;
- a second front portion having a first side edge and a second side edge, said first side edge connected to said second side edge of said back portion and a substantially U-shaped second underarm flap with an open upper side and coupled to a top edge of said second front portion and said back portion and having a tube arranged in a circuitous pattern for receiving the cooled water and having an inlet and an outlet connected to said cooling unit for cooling a front side and underarm of said patient;

a first shoulder flap having a first edge connected to said top edge of said back portion adjacent said first side edge of said back portion and having a tube arranged in a circuitous pattern for receiving said cooled water and having an inlet and an outlet, said first shoulder flap being positioned for folding over a first shoulder of said patient and removably fastening to said first front portion by a fastener and cooling a shoulder of said patient;

a second shoulder flap having a first edge connected to a top edge of said back portion adjacent said second side edge of said back portion and positioned for folding over a second shoulder of said patient and removably fastening to said second front portion by a fastener, said second shoulder flap having a tube arranged in a circuitous pattern to receive the cooled water for cooling a shoulder of said patient;

a hood attached to said top edge of said back portion, said hood having opposite first and second side portions, a top portion and a chin strap forming a neck portion attached to said first side portion and having a length to wrap around a front portion of the neck of the patient and removably fastened to the second side portion by a fastener for covering the front and sides of the neck of the patient, and a cooling tube arranged in a circuitous pattern through said side portions, top portion and chin strap of said hood for cooling the sides and top of the head of the patient and for cooling the front and sides of the neck of the patient;

a bottom flap coupled to a bottom edge of said second front portion and positioned for folding under the groin of the patient and removably fastened to said bottom edge of said back portion by a fastener, said bottom flap including a tube for arranging in a circuitous pattern for receiving said cooled water; and a supply tube having a first feed tube connecting the outlet of the cooling unit to the cooling garment, a second feed tube connecting the inlet of the cooling unit to the cooling garment for directing cooled water through the cooling garment, and an insulating sleeve surrounding the first and second feed tubes.

\* \* \* \* \*